United States Patent
Dai et al.

(10) Patent No.: US 11,992,513 B2
(45) Date of Patent: May 28, 2024

(54) TRADITIONAL CHINESE MEDICINE COMPOSITION FOR TREATING HAND-FOOT SYNDROME (HFS) AFTER TARGETED DRUG TREATMENT AND METHOD FOR MAKING THE SAME

(71) Applicant: THE AFFILIATED HOSPITAL OF JIANGXI UNIVERSITY OF TCM, Nanchang (CN)

(72) Inventors: Qi Dai, Nanchang (CN); Kunshan Chen, Nanchang (CN); Xiaoqi Zhou, Nanchang (CN)

(73) Assignee: THE AFFILIATED HOSPITAL OF JIANGXI UNIVERSITY OF TCM, Nanchang (CN)

( * ) Notice: Subject to any disclaimer, the term of this patent is extended or adjusted under 35 U.S.C. 154(b) by 0 days.

(21) Appl. No.: 17/953,859

(22) Filed: Sep. 27, 2022

(65) Prior Publication Data
US 2023/0321172 A1    Oct. 12, 2023

(30) Foreign Application Priority Data
Mar. 28, 2022 (CN) .......................... 202210315505.1

(51) Int. Cl.
| | | |
|---|---|---|
| A61K 36/489 | (2006.01) | |
| A61K 36/17 | (2006.01) | |
| A61K 36/21 | (2006.01) | |
| A61K 36/236 | (2006.01) | |
| A61K 36/24 | (2006.01) | |
| A61K 36/258 | (2006.01) | |
| A61K 36/286 | (2006.01) | |
| A61K 36/287 | (2006.01) | |
| A61K 36/288 | (2006.01) | |
| A61K 36/31 | (2006.01) | |
| A61K 36/481 | (2006.01) | |
| A61K 36/484 | (2006.01) | |
| A61K 36/54 | (2006.01) | |
| A61K 36/804 | (2006.01) | |
| A61K 36/86 | (2006.01) | |
| A61K 36/8884 | (2006.01) | |
| A61K 36/90 | (2006.01) | |
| A61P 17/00 | (2006.01) | |

(52) U.S. Cl.
CPC ............ *A61K 36/489* (2013.01); *A61K 36/17* (2013.01); *A61K 36/21* (2013.01); *A61K 36/236* (2013.01); *A61K 36/24* (2013.01); *A61K 36/258* (2013.01); *A61K 36/286* (2013.01); *A61K 36/287* (2013.01); *A61K 36/288* (2013.01); *A61K 36/31* (2013.01); *A61K 36/481* (2013.01); *A61K 36/484* (2013.01); *A61K 36/54* (2013.01); *A61K 36/804* (2013.01); *A61K 36/86* (2013.01); *A61K 36/8884* (2013.01); *A61K 36/90* (2013.01); *A61P 17/00* (2018.01)

(58) Field of Classification Search
None
See application file for complete search history.

(56) References Cited

FOREIGN PATENT DOCUMENTS

| CN | 113144034 A | * | 7/2021 |
| CN | 113209238 A | * | 8/2021 |
| CN | 114306478 A | * | 4/2022 |

OTHER PUBLICATIONS

Zhao, C., et al., Effect of modified Taohongsiwu decoction on patients with chemotherapy-induced hand-foot syndrome, J Tradit Chin Med Feb. 15, 2014; 34(1): 10-14 (Year: 2014).*
Deng, B. & Sun, W., Herbal medicine for hand-foot syndrome induced by fluoropyrimidines: A systematic review and meta-analysis, Phytotherapy Research. 2018;32:1211-1228 (Year: 2018).*
Shao, Y., et al., Chrysanthemum indicum L.: A Comprehensive Review of its Botany, Phytochemistry and Pharmacology (abstract), The American Journal of Chinese Medicine vol. 48 No. 04 (May 20, 2020), available at https://www.worldscientific.com/doi/epdf/10.1142/S0192415X20500421 (Year: 2020).*
Fan, Y.P. & Xiong, X.J., [Chinese classical formulas Ephedra associated prescriptions for treatment of skin diseases] (abstract), China Journal of Chinese Materia Medica, Jun. 1, 2018, 43(12):2431-243 (Year: 2018).*
Yuan, H., et al., Mustard seeds (*Sinapis alba* Linn) attenuate azoxymethane-induced colon carcinogenesis, Redox Report 2011 vol. 16 38-44) (Year: 2011).*
Wang, C., et al., De novo sequencing and transcriptome assembly of Arisaema heterophyllum Blume and identification of genes involved in isoflavonoid biosynthesis, Scientific Reports vol. 8, Article No. 17643 (2018) (Year: 2018).*

(Continued)

*Primary Examiner* — H. Sarah Park
(74) *Attorney, Agent, or Firm* — Edell, Shapiro & Finnan, LLC

(57) ABSTRACT

A traditional Chinese medicine composition for treating hand-foot syndrome after targeted drug treatment is mainly prepared from the following components by weight: 20-50 parts of *Radix Sophorae Flavescentis*, 20-50 parts of *Herba Taraxaci*, 20-50 parts of *Flos Chrysanthemi Indici*, and 20-50 parts of *Herba* Cum Radice *Violae* Yedoensitis, 20-50 parts of *Rhizoma Smilacis Glabrae*, 30-60 parts of *Radix Astragali* Seu *Hedysari*, 10-35 parts of *Kochia scoparia* (L.) Schrad, 10-45 parts of *Carthamus tinctorius* L., 15-45 parts of *Cortex Radicis Dictamni Dasycarpi*, 5-15 parts of *Herba Ephedrae*, 5-25 parts of *Angelica sinensis*, 5-25 parts of *Rhizoma Ligustici* Chuangxiong, 10-30 parts of *Radix Rehmanniae*, 5-15 parts of *Ramulus cinnamomi*, 10-30 parts of *Cynanchum otophyllum* Schneid, 5-15 parts of *Semen Sinapis Albae*, 5-20 parts of *Arisaema heterophyllum* Blume, 5-20 parts of *Typhonium blumei* Nicolson & Sivadasan, and 10-40 parts of *Radix Glycyrrhizae*.

13 Claims, 1 Drawing Sheet

(56) References Cited

OTHER PUBLICATIONS

Khalivulla, S., et al., Novel Phytochemical Constituents and Anti-cancer Activities of the Genus (abstract), *Typhonium*, Current Drug Metabolism, vol. 20, No. 12 (2019) 946-57 (Year: 2019).*
Machine translation of CN 113144034A (Year: 2023).*
Machine translation of CN 113209238A (Year: 2023).*
Machine translation of CN 114306478A (Year: 2023).*

* cited by examiner

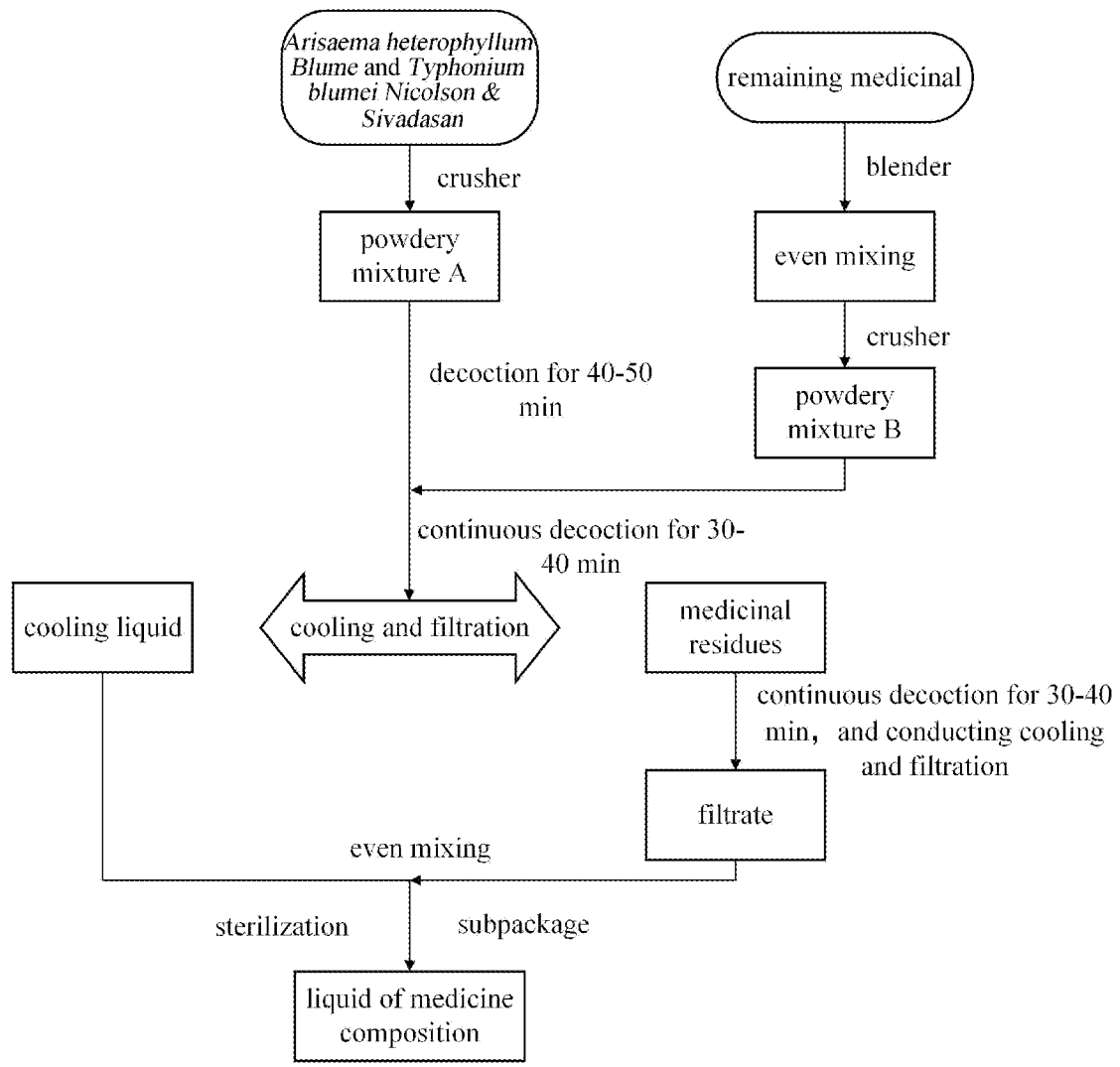

TRADITIONAL CHINESE MEDICINE COMPOSITION FOR TREATING HAND-FOOT SYNDROME (HFS) AFTER TARGETED DRUG TREATMENT AND METHOD FOR MAKING THE SAME

CROSS REFERENCE TO RELATED APPLICATION

This patent application claims the benefit and priority of Chinese Patent Application No. 202210315505.1, entitled "Traditional Chinese medicine composition for treating hand-foot syndrome (HFS) after targeted drug treatment and method for making the same" filed on Mar. 28, 2022, the disclosure of which is incorporated by reference herein in its entirety as part of the present application.

TECHNICAL FIELD

The disclosure belongs to the technical field of traditional Chinese medicine, in particular to a traditional Chinese medicine composition for treating HFS after targeted drug treatment and a method for making the same.

BACKGROUND ART

Malignant tumor is a multi-system refractory disease with low survival rate and poor prognosis, and that originated from epithelial tissue is called cancer. In 2020, the number of new cancer cases in China was 4.57 million, where most patients received targeted drug treatment. However, treatment of targeted drug such as sorafenib, sunitinib, etc., brings a side effect that obviously affects the patient's life quality, that is hand-foot syndrome (HFS). HFS is manifested as palmoplantarerythrodysesthesia, acroerythema, chemotherapy-induced acroerythema, palmar and plantar (palmplantar) sensory loss, palmar and plantar erythema, palmar and plantar erythroderma, toxicity erythema, etc., and characterized by numbness, hypoesthesia, paresthesia, tingling, anodynia or analgesia, swelling or erythema of the skin, peeling, rhagade, induration-like blisters or severe pain in the extremity of hand and foot, etc. There is no systematic treatment for HFS in the existing western medicine diagnosis and treatment standards. Western medicine recommends oral vitamin, as well as topical vaseline ointment or skin care products for symptomatic treatment. The treatment effect is poor and varies from person to person, with a frequent recurrence. Therefore, subjects may terminate targeted drug treatment due to intolerance of HFS.

There are certain advantages in the prevention and treatment of HFS by traditional Chinese medicine, because it not only can reconcile the internal yin and yang as well as cold and heat through oral medication of traditional Chinese medicine decoction, but also improve local symptoms of HFS through topical treatment of traditional Chinese medicine to cooperate with targeted drug treatment. Common topical medication with traditional Chinese medicine include topical application of ointment and decoction fumigation, in which the ointment includes Yan-di-oil (mainly composed of *Radix* arneblae, Stragalus *Membranaceus* (Fisch.) Bunge, and *Radix Angelicae* Sinesis, etc.), moisture exposed burn ointment (*Coptidis Chinensis* Franch, *Phellodendron Chinense* schneid, *Scutellaria baicalensis Georgi*, *Radix* arneblae, *Anemone Altaica* Fisch, *Angelica dahurica* (Fisch. ex Hoffm.) Benth. et Hook. f. ex Franch. et Say, Pernulo, borax, and Borneolum, etc.), etc.; the decoctions include: Zhigui Tongluo Decoction (Stragalus *membranaceus* (Fisch.) Bunge, *Ramulus cinnamomi*, *Radix* arneblae, *Chaenomeles speciosa* (Sweet) Nakai, *Curcuma longa* L., *Angelica sinensis*, *Asarum sieboldii* Miq., *Carthamus tinctorius* L., and *Aconitum carmichaeli* Debx.); Simiao Huoxue San (*Phellodendron Chinense* schneid, *Atractylodes Lancea* (Thunb.) DC., raw *Coix lacryma-jobi* L. var.mayuen (Roman.) Stapf, *Cyathula officinalis Kuan*, *Semen Pruni Persicae*, *Carthamus tinctorius* L., *Caesalpinia sappan* L. and *Lycopodium jaPonicum* Thunb.), Huangzhi Guizhi Wuwu Decoction (Stragalus *Membranaceus* (Fisch.) Bunge, *Ramulus cinnamomi*, *Angelica sinensis*, *Caulis Piperis* Futokadsurae, *Carthamus tinctorius* L., *Radix Rubrus Paeoniae* Lactiflorae, and *Cynanchum otophyllum* Schneid.), Taohong Siwu Decoction with addictives (*Semen Pruni Persicae*, prepared *Carthamus tinctorius* L., *Rehmannia glutinosa* (Gaetn.) Libosch. ex Fisch. et Mey., *Angelica sinensis*, *Cortex Ailanthi Ailanthus altissima* (Mill.) Swingle, *Ramulus cinnamomi*, *Cyathula officinalis Kuan*, *Radix Glycyrrhizae*., and *Fructus Zizyphi Jujubae*) and so on. However, the therapeutic effect needs to be improved. Therefore, the development of a traditional Chinese medicine composition for treating HFS after targeted drug treatment is of great significance for the characteristic treatment of HFS in traditional Chinese medicine.

SUMMARY

The technical problem of the present disclosure is how to overcome the deficiencies in the prior art, and a traditional Chinese medicine composition for treating HFS after targeted drug treatment and a method for making the same are provided.

A first aspect of the technical solution of the present disclosure includes:

a traditional Chinese medicine composition for treating HFS after targeted drug treatment, which is mainly prepared from the following components by weight:

20-50 parts of *Radix Sophorae Flavescentis*, 20-50 parts of *Herba Taraxaci*, 20-50 parts of *Flos Chrysanthemi Indici*, 20-50 parts of *Herba* Cum Radice *Violae* Yedoensitis, 20-50 parts of *Rhizoma Smilacis Glabrae*, 30-60 parts of *Radix Astragali* Seu *Hedysari*, 10-35 parts of *Kochia scoparia* (L.) Schrad, 10-45 parts of *Carthamus tinctorius* L., 15-45 parts of *Cortex Radicis Dictamni Dasycarpi*, 5-15 parts of *Herba Ephedrae*, 5-25 parts of *Angelica sinensis*, 5-25 parts of *Rhizoma Ligustici* Chuangxiong, 10-30 parts of *Radix Rehmanniae*, 5-15 parts of *Ramulus cinnamomi* 10-30 parts of *Cynanchum otophyllum* Schneid, 5-15 parts of *Semen Sinapis Albae*, 5-20 parts of *Arisaema heterophyllum* Blume, 5-20 parts of *Typhonium blumei* Nicolson & Sivadasan, and 10-40 parts of *Radix Glycyrrhizae*.

In some embodiments, a mass ratio between the *Radix Sophorae Flavescentis* and the *Rhizoma Smilacis Glabrae* is 1:1.

In some embodiments, a mass ratio among the *Flos Chrysanthemi Indici*, *Herba Taraxaci* and *Herba* Cum Radice *Violae* Yedoensitis is 1:1:1.

In some embodiments, a mass ratio between the *Angelica sinensis* and the *Rhizoma Ligustici* Chuangxiong is 1:1.

In some embodiments, a mass ratio among the *Arisaema heterophyllum* Blume, the *Typhonium blumei* Nicolson & Sivadasan and the *Radix Glycyrrhizae* is 1:1:2.

A second aspect of the technical solution of the present disclosure includes: a method for preparing the traditional Chinese medicine composition for treating HFS after targeted drug treatment, including the following steps:
(1) weighing medicinal materials according to a formula;
(2) crushing the *Arisaema heterophyllum* Blume and the *Typhonium blumei* Nicolson & Sivadasan into a powdery mixture A; stirring, mixing, and then crushing remaining medicinal materials into a powdery mixture B according to the formula;
(3) after adding water to the powdery mixture A for a period of decoction, adding the powdery mixture B for a period of continuous decoction, and conducting cooling and filtration to obtain a cooling liquid and medicinal residues;
(4) adding water to the medicinal residues for a secondary decoction, and conducting cooling and filtration to obtain a filtrate; and
(5) combining the cooling liquid in step (3) and the obtained filtrate in step (4), and conducting sterilization and encapsulation to obtain the traditional Chinese medicine composition for treating HFS after targeted drug treatment.

In some embodiments, in step (3), after added with water, the powder mixture A is heated to boiling for 40-50 min.

In some embodiments, in step (3), the powdery mixture B is added for decoction for 30-40 min.

In some embodiments, in step (4), the secondary decocting is a decodction for 30-40 min after a heating until boiling.

The traditional Chinese medicine composition for treating HFS after targeted drug treatment of the present disclosure, including principal drugs, *Radix Sophorae Flavescentis* and *Radix Astragali* Seu *Hedysari* to clear heat and dry dampness, tonify qi and strengthen body defence; minister drugs, *Cortex Radicis Dictamni Dasycarpi* and *Kochia scoparia* (L.) Schrad to dispel wind to eliminate dampness, *Rhizoma Smilacis Glabrae* to detoxify and dehumidify, *Angelica sinensis, Carthamus tinctorius* L., *Rhizoma Ligustici* Chuangxiong and *Radix Rehmanniae* to nourish blood and active blood; assistant drugs, *Herba Ephedrae* and *Ramulus cinnamomi* to open striae, *Cynanchum otophyllum* Schneid to nourish blood and relieve pain, *Semen Sinapis Albae, Arisaema heterophyllum* Blume and *Typhonium blumei* Nicolson & Sivadasan to dry dampness to reduce phlegm; guid drugs, *Radix Glycyrrhizae* to coordinate the drug actions above and to treat the toxicity of *Arisaema heterophyllum* Blume and *Typhonium blumei* Nicolson & Sivadasan. The whole formula plays the functions of tonifying qi and nourishing blood, clearing heat and detoxifying, drying dampness to reduce phlegm, and has a significant effect on the treatment of HFS after targeted drug treatment. Traditional Chinese medicine believes that the development mechanism of HFS is that after targeted drugs are used to treat malignant tumors, the body's qi and blood are deficient, the heat toxin are accumulated and cannot be eliminated in the body, and phlegm-dampness is also present in the body. Topical treatment of traditional Chinese medicine can be administered through the body surface near the lesions, besides, which has the functions of tonifying qi and nourishing blood, clearing heat and toxic material, drying dampness and reducing phlegm, thereby relieving HFS after targeted drug treatment.

Compared with the prior art, the advantages of the present disclosure are:

The traditional Chinese medicine composition of the present disclosure can be used for the hand-foot skin reaction sites after the targeted drug treatment, with the effects of tonifying qi and nourishing blood, clearing heat and toxic material, drying dampness and reducing phlegm, and has a good therapeutic effect on the HFS after targeted drug treatment, which is simple, convenient, low-cost and easy to implement.

BRIEF DESCRIPTION OF THE DRAWINGS

FIG. 1 shows a process flow diagram of the present disclosure for preparing a traditional Chinese medicine composition for treating HFS after targeted drug treatment.

DETAILED DESCRIPTION OF THE EMBODIMENTS

In order to facilitate the understanding of the present disclosure, the embodiments will be described more comprehensively and in detail below with reference to the drawings and examples, but the claimed scope herein is not limited to the following specific embodiments.

In the detailed description of the embodiment herein, the traditional Chinese medicine composition for treating HFS after targeted drug treatment is mainly prepared from the following components by weight: 20-50 parts of *Radix Sophorae Flavescentis*, 20-50 parts of *Herba Taraxaci*, 20-50 parts of *Flos Chrysanthemi Indici*, 20-50 parts of *Herba* Cum Radice *Violae* Yedoensitis, 20-50 parts of *Rhizoma Smilacis Glabrae*, 30-60 parts of *Radix Astragali* Seu *Hedysari*, 10-35 parts of *Kochia scoparia* (L.) Schrad, 10-45 parts of *Carthamus tinctorius* L., 15-45 parts of *Cortex Radicis Dictamni Dasycarpi*, 5-15 parts of *Herba Ephedrae*, 5-25 parts of *Angelica sinensis*, 5-25 parts of *Rhizoma Ligustici* Chuangxiong, 10-30 parts of *Radix Rehmanniae*, 5-15 parts of *Ramulus cinnamomi* 10-30 parts of *Cynanchum otophyllum* Schneid, 5-15 parts of *Semen Sinapis Albae*, 5-20 parts of *Arisaema heterophyllum* Blume, 5-20 parts of *Typhonium blumei* Nicolson & Sivadasan, and 10-40 parts of *Radix Glycyrrhizae*. A mass ratio between the *Radix Sophorae Flavescentis* and the *Rhizoma Smilacis Glabrae* is 1:1; a mass ratio among the *Flos Chrysanthemi Indici, Herba Taraxaci* and *Herba* Cum Radice *Violae* Yedoensitis is 1:1:1; a mass ratio between the *Angelica sinensis* and the *Rhizoma Ligustici* Chuangxiong is 1:1; a mass ratio among the *Arisaema heterophyllum* Blume, the *Typhonium blumei* Nicolson & Sivadasan and the *Radix Glycyrrhizae* is 1:1:2.

In the detailed description of the embodiment herein, a method for preparing the traditional Chinese medicine composition for the treatment of HFS after targeted drug treatment, the process flow chart of which is shown in FIG. 1, and includes the following steps:
(1) weighing medicinal materials according to a formula;
(2) crushing the *Arisaema heterophyllum* Blume and the *Typhonium blumei* Nicolson & Sivadasan into a powdery mixture A; stirring, mixing and then crushing remaining medicinal materials into a powdery mixture B according to the formula;
(3) adding water to the powdery mixture A, conducting heating to 100° C., followed by decoction for 40-50 min, then adding the powdery mixture B for decoction for 30-40 min, and conducting cooling and filtration to obtain a cooling liquid and medicinal residues;
(4) adding water to the medicinal residues, conducting heating to 100° C. for continuous decoction for 30-40 min, and conducting cooling and filtration to obtain a filtrate; and
(5) combining the cooling liquid in step (3) and the obtained filtrate in step (4), and conducting sterilization and encapsulation to obtain a traditional Chinese medicine composition for treating HFS after targeted drug treatment.

In order to prove the effect of the traditional Chinese medicine composition of the present disclosure, a randomized double-blind trial research design is adopted, and a clinical study on the treatment of HFS is carried out in the Affiliated Hospital of Jiangxi University of Traditional Chinese Medicine. There are 42 cases in the test group and 42 cases in the control group. 200 mL of the traditional Chinese medicine composition liquid in Example 1 of the present disclosure is used to soak and wash the affected part, twice a day in the test group; 200 mL of common extract of *artemisia argyi* liquid is used to soak and wash the affected part, twice a day in the control group; the observation time for both of the two groups is 2 weeks.

The main contents of the experiment are as follows:

1. Materials and Methods 1.1 Clinical Design

A random, double-blind, and controlled design is adopted and completed in the Affiliated Hospital of Jiangxi University of Traditional Chinese Medicine. The cases are mainly from inpatient and outpatient tumor patients in the hospital, and 60 cases of effective patient data are selected. The traditional Chinese medicine composition according to the present disclosure is used for the treatment of HFS in the early stage with a cure rate of 83%. And the cure rate of the control group is 46%, as reported by previous literature.

1.2 Case Selection 1.2.1 Diagnostic Criteria 1.2.1.1 Western Medicine Diagnostic Criteria The diagnostic criteria of tumors can be found in "Chinese standard for diagnosis and treatment of common malignant tumor" by the Department of Medical Administration, Ministry of Health of the People's Republic of China, and the staging criteria are based on "NCCN Clinical practice guidelines (Chinese version), 2012, 1st edition": HFS grading criteria can be found in the grading criteria for acute and subacute toxicity of anticancer drug formulated by National Cancer Institute (NCI).

Grading criteria for HFS according to NCI:

grade I: minor skin changes or dermatitis (e.g., erythema, desquamation) with paresthesias (e.g., numbness, tingling, burning), without affecting daily activities;

grade II: skin changes as above accompanied by pain that mildly affect daily activities, with intact skin surface;

grade III: ulcerative dermatitis or skin changes, accompanied by severe pain that seriously affect daily life, with obvious tissue destruction (such as peeling, blisters, bleeding, edema).

1.2.1.2 Diagnostic Criteria of Traditional Chinese Medicine

Qi deficiency syndrome: dim skin of the affected part, short breath, low voice, mental fatigue, and hypodynamia; lack of strength to breath or talk; spontaneous sweating; pale and swollen tongue or tongue with teeth prints; empty pulse with little strength (weak, soft and float), with or without light-headedness. And movement may aggravate all symptoms above.

Blood deficiency syndrome: pale skin of the affected area, less obvious changes in dermatitis, pale or sallow complexion, pale eyelids, lips, tongue, and nails, and head dizziness, with or without blurred vision, dry eyes, palpitations, dreaminess, forgetfulness, mental fatigue, numbness in hands and feet, or hypomenorrhea, pale color of menstrual blood, delayed or disappeared menstruation, thin and weak pulse.

Damp-heat syndrome: sweaty affected area, frequent feeling of dampness, fullness in the flanks, emotional discomfortness, dry mouth and bitter taste, abdominal distension, loose stools, unpleasantness, difficulty in micturition, red and short urine with pain, yellow and greasy fur, stringy and slippery pulse.

Phlegm-dampness syndrome: swollen affected part that is depressed when pressed; cough with excessive phlegm, chest tightness and epigastric fullness, anorexia; dull complexion, feeling of heaviness in the head and body, with or without edema of lower extremities; sticky stool, slippery pulse (stringy, float), greasy and slippery fur of tongue.

Toxin and stasis syndrome: dull even purple-black skin of the affected area, with symptoms such as pain, lump, bleeding, and blood stasis-colored pulse. The pain of toxin and stasis syndrome is characterized by tingling, refusal to press and immobility of the sore; dull complexion, violaceous lips and nails, or purple spots on the subcutaneous, or scaly dry skin, or prominent abdominal veins, or filamentous red strands on the skin, or purple spots on the tongue, sublingual varicose veins, with thin or uneven pulse, or knotted and intermittent pulse, pulselessness and so on.

1.3 Test Drugs and Drug Assignment 1.3.1 Test Drugs

Test group: 200 mL of the traditional Chinese medicine composition liquid of Example 1 of the present disclosure is used to soak and wash the affected part, twice a day.

Control group: 200 mL of common extract of *Artemisia argyi* liquid is used to soak and wash the affected part, twice a day in the control group.

Both groups are intervened for 14 days.

1.3.2 Drug Assignment

The patients will be randomly divided into the test group and the control group according to the ratio of 1:1, and the observing doctors will assign the drugs according to the drug's number without selecting the medicine and disturbing the number, and the drug's number remains constant during test.

1.3.3 Drug Check

At each follow-up visit, the number of drugs received, taken and returned by the patient in detail are recorded timely on the case report form by the observing doctor to determine the compliance of the subjects taking the drug, and to decide whether the patient continues to participate in the test. A patient is considered to be in good compliance if he undertakes regularly medication according to the protocol and reaches 80% of the required dose at each evaluation.

1.3.4 Provisions for Concomitant Medication

① During the test period, no other drugs for the treatment of HFS should be used.

② When combined with other drugs and therapeutic methods that must be taken or adopted for other diseases, the original treatment are still maintained after enrollment but must be recorded in detail in the combined medication table.

1.4 Adverse Reactions and Safety Evaluation

Grade 1: no adverse reactions and no abnormality in safety indicators appear;

grade 2: tolerable minor adverse reactions are present, no additional treatment is required, and there is no abnormality in safety indicators;

grade 3: the subjects have moderate adverse reactions that require appropriate treatment, and the safety indicators is mildly or moderately abnormal;

grade 4: the subjects have severe adverse reactions that are life-threatening or disabled, and need urgent treatment. The safety indicators are seriously abnormal, such that the treatment study should be interrupted immediately.

1.5 Statistical Processing

SPSS26 software are used for statistical analysis. Measurement data were described as mean±standard deviation. T test is performed on data with normal distribution and homogeneity of variance, analysis of variance (ANOVA) is performed on those without homogeneity of variance, and rank sum test is performed on those without normal distribution and on ranked data. Two-sided test is performed on all the analyzed results. $P>0.05$ indicates that the difference between the compared two is not statistically significant, and $P<0.05$ indicates the difference is statistically significant.

2. Efficacy Evaluation after Two Weeks of Treatment

As seen from the improvement of HFS symptom in Table 1, the HFS symptoms of patients taking the traditional Chinese medicine composition of the present disclosure are significantly improved.

TABLE 1

Improvement of HFS Symptom

| Index | Group | Number of case | Mean | Standard deviation | Max | Min | Statistic | P value | Statistic | P value |
|---|---|---|---|---|---|---|---|---|---|---|
| Insensitivity | Experimental group | 30 | 2.900 | 1.777 | 5 | 0 | 87 | 0.003 | 4.678 | <0.05 |
|  | Control group | 30 | 0.867 | 1.500 | 4 | −3 | 26 | 0.207 |  | <0.05 |
| Numbness | Experimental group | 30 | 7.033 | 1.426 | 10 | 5 | 211 | 0.043 | 4.826 | <0.05 |
|  | Control group | 30 | 3.567 | 1.627 | 8 | 1 | 107 | 0.077 |  | <0.05 |
| Tingling | Experimental group | 30 | 6.533 | 1.979 | 9 | 1 | 196 | 0.006 | 4.816 | <0.05 |
|  | Control group | 30 | 2.800 | 2.301 | 7 | −2 | 84 | 0.514 |  | <0.05 |
| Burning | Experimental group | 30 | 5.600 | 2.169 | 10 | 2 | 168 | 0.105 | 4.677 | <0.05 |
|  | Control group | 30 | 3.233 | 1.944 | 7 | −1 | 97 | 0.541 |  | <0.05 |
| Swelling | Experimental group | 30 | 3.500 | 2.432 | 10 | 1 | 105 | 0.001 | 4.859 | <0.05 |
|  | Control group | 30 | 1.467 | 2.045 | 8 | −2 | 44 | 0.001 |  | <0.05 |
| Pruritus | Experimental group | 30 | 7.433 | 1.764 | 10 | 4 | 223 | 0.031 | 4.841 | <0.05 |
|  | Control group | 30 | 3.900 | 1.660 | 7 | 0 | 117 | 0.252 |  | <0.05 |
| Pain | Experimental group | 30 | 3.800 | 1.661 | 7 | 1 | 114 | 0.068 | 4.687 | <0.05 |
|  | Control group | 30 | 1.733 | 1.843 | 5 | −2 | 52 | 0.162 |  | <0.05 |
| Erythema | Experimental group | 30 | 2.933 | 1.289 | 5 | 1 | 88 | 0.004 | 4.766 | <0.05 |
|  | Control group | 30 | 1.033 | 1.378 | 4 | −2 | 31 | 0.265 |  | <0.05 |
| HFS total score | Experimental group | 30 | 4.967 | 2.559 | 10 | 0 | 1192 | 0.002 | 13.336 | <0.05 |
|  | Control group | 30 | 2.325 | 2.126 | 8 | −3 | 558 | 0.001 |  | <0.05 |

The cases in the following examples are all from patients with HFS after targeted drug treatment of malignant tumors from January 2010 to November 2021. For the diagnostic criteria of tumors, see "Chinese standard for diagnosis and treatment of common malignant tumor". The HFS grading criteria for HFS are as follows (see the grading criteria for acute and subacute toxicity of anticancer drug formulated by NCI):

grade I: minor skin changes or dermatitis (eg, erythema, desquamation) with paresthesias (eg, numbness, tingling, burning), without affecting daily activities;

grade II: skin changes accompanied by pain as above that mildly affect daily activities, with intact skin surface;

grade III: ulcerative dermatitis or skin changes, accompanied by severe pain that seriously affect daily life, with obvious tissue destruction (such as peeling, blisters, bleeding, edema).

Example 1

A traditional Chinese medicine composition for treating HFS after targeted drug treatment was mainly prepared from the following components by weight: 30 parts of *Radix Sophorae Flavescentis*, 50 parts of *Herba Taraxaci*, 50 parts of *Flos Chrysanthemi Indici*, and 50 parts of *Herba* Cum Radice *Violae* Yedoensitis, 30 parts of *Rhizoma Smilacis Glabrae*, 30 parts of *Radix Astragali* Seu *Hedysari*, 15 parts of *Kochia scoparia* (L.) Schrad, 20 parts of *Carthamus tinctorius* L., 20 parts of *Cortex Radicis Dictamni Dasycarpi*, 5 parts of *Herba Ephedrae*, 10 parts of *Angelica sinensis*, 10 parts of *Rhizoma Ligustici* Chuangxiong, 15 parts of *Radix Rehmanniae*, 5 parts of *Ramulus cinnamomi*, 10 parts of *Cynanchum otophyllum* Schneid, 5 parts of *Semen Sinapis Albae*, 5 parts of *Arisaema heterophyllum* Blume, 5 parts of *Typhonium blumei* Nicolson & Sivadasan, and 10 parts of *Radix Glycyrrhizae*.

The method for preparing the traditional Chinese medicine composition for the treatment of HFS after targeted drug treatment of the present example was carried out as follows:

(1) the medicinal materials was weighted according to the formula;

(2) the *Arisaema heterophyllum* Blume and the *Typhonium blumei* Nicolson & Sivadasan were crushed into a powdery mixture A; the other medicinal materials according to the formula were stirred, mixed, then crushed into a powdery mixture B;

(3) the powdery mixture A was added with distilled water 10 times of its volume, heated to 100° C., and decocted continuously for 40 min, then the powdery mixture B was added, and a resulting mixture was decocted continuously for 40 min, cooled and filtered to obtain a cooling liquid and medicinal residues;
(4) the medicinal residues were added with distilled water 8 times of its volume, heated to 100° C., decocted continuously for 40 min, cooled and then filtered to obtain a filtrate; and
(5) the cooling liquid in step (3) and the filtrate in step (4) were combined, and a resulting mixed filtrate was centrifuged at 4000 g for 10 minutes at room temperature, a supernatant was collected, and the supernatant was concentrated to 1 g/ml, a resulting medicine solution was yellowish-brown, and had strong smell of traditional Chinese medicine, after sterilization and encapsulation, a traditional Chinese medicine composition for treating HFS after targeted drug treatment was obtained. The obtained traditional Chinese medicine had a liquid pharmaceutical dosage form.

80 cases were selected, including 44 males and 36 females. The youngest patient was 35 years old and the oldest was 82 years old, with an average age of 53 years. The cases were randomly divided into 8 groups according to age and condition, with 10 cases in each group. Efficacy was judged based on HFS grading, in which skin changes or dermatitis, paresthesias, and tissue destruction took the first place.

The traditional Chinese medicine composition of this example was used for treatment, and the dosage was as follows: for patients of 35-55 years old, 200 ml was used for each fumigation and wash of the affected part once a day; for patients of 56-82 years old, 200 ml was used for each fumigation and wash of the affected part twice a day. After one week of fumigation and washing, the HFS grade of 72% of the patients was decreased by one level (level 3 was decreased to level 2, and level 2 was decreased to level 1). After two weeks of fumigation and washing, 85% of patients with skin changes or dermatitis returned to normal basically, and sensory abnormalities disappeared basically. No obvious adverse reactions appeared in patients during the treatment, and no adverse reactions of the test medicine were observed.

Example 2

A traditional Chinese medicine composition for treating HFS after targeted drug treatment was mainly prepared from the following components by weight: 50 parts of *Radix Sophorae Flavescentis*, 25 parts of *Herba Taraxaci*, 25 parts of *Flos Chrysanthemi Indici*, and 25 parts of *Herba* Cum Radice *Violae* Yedoensitis, 50 parts of *Rhizoma Smilacis Glabrae*, 35 parts of *Radix Astragali* Seu *Hedysari*, 35 parts of *Kochia scoparia* (L.) Schrad, 20 parts of *Carthamus tinctorius* L., 45 parts of *Cortex Radicis Dictamni Dasycarpi*, 5 parts of *Herba Ephedrae*, 15 parts of *Angelica sinensis*, 15 parts of *Rhizoma Ligustici* Chuangxiong, 10 parts of *Radix Rehmanniae*, 5 parts of *Ramulus cinnamomi*, 15 parts of *Cynanchum otophyllum* Schneid, 5 parts of *Semen Sinapis Albae*, 10 parts of *Arisaema heterophyllum* Blume, 10 parts of *Typhonium blumei* Nicolson & Sivadasan, and 10 parts of *Radix Glycyrrhizae*.

The method for preparing the traditional Chinese medicine composition for the treatment of HFS after targeted drug treatment of the present example was carried out as follows:
(1) the medicinal materials was weighted according to the formula;
(2) the *Arisaema heterophyllum* Blume and the *Typhonium blumei* Nicolson & Sivadasan were crushed into a powdery mixture A; the other medicinal materials according to the formula were stirred, mixed, then crushed into a powdery mixture B;
(3) the powdery mixture A was added with distilled water 10 times of its volume, heated to 100° C., and decocted continuously for 45 min, then the powdery mixture B was added, decocted continuously for 40 min, cooled and filtered to obtain a cooling liquid and medicinal residues;
(4) the medicinal residues were added with distilled water 8 times of its volume, heated to 100° C., decocted continuously for 35 min, cooled and then filtered to obtain a filtrate; and
(5) the cooling liquid in step (3) and the filtrate in step (4) were combined, and a resulting mixed filtrate was centrifuged at 4000 g for 10 minutes at room temperature, a supernatant was collected for vacuum concentration at 60° C., a resulting extract was freeze-dried to powder, and stored at −20° C. A traditional Chinese medicine composition for treating HFS after targeted drug treatment was obtained. The obtained traditional Chinese medicine had a pharmaceutical dosage form of Semi-solid powdered mixture. The powder was dissolved in water of equal volume, then heated to 45° C., mixed evenly for use. A resulting medicine solution was yellowish-brown, and had strong smell of traditional Chinese medicine.

70 cases were selected, including 38 males and 32 females. The youngest patient was 32 years old and the oldest was 65 years old, with an average age of 45 years. The cases were randomly divided into 7 groups according to age and condition, with 10 cases in each group. Efficacy was judged based on HFS grading, in which skin changes or dermatitis, paresthesias, and tissue destruction took the first place.

The traditional Chinese medicine composition of this example was used for treatment, and the dosage was as follows: for patients of 32-48 years old, 200 ml was used once a day to fumigate and wash the affected part each time; for patients of 49-65 years old, 200 ml was used for each fumigation and wash of the affected part twice a day. After one week of fumigation and washing, the HFS grade of 75% of the patients was decreased by one level (level 3 was decreased to level 2, and level 2 was decreased to level 1). After two weeks of fumigation and washing, 82% of patients with skin changes or dermatitis returned to normal basically, and sensory abnormalities disappeared basically. No obvious adverse reactions appeared in patients during the treatment, and no adverse reactions of the test medicine were observed.

Example 3

A traditional Chinese medicine composition for treating HFS after targeted drug treatment was mainly prepared from the following components by weight: 25 parts of *Radix Sophorae Flavescentis*, 35 parts of *Herba Taraxaci*, 35 parts of *Flos Chrysanthemi Indici*, and 35 parts of *Herba* Cum Radice *Violae* Yedoensitis, 25 parts of *Rhizoma Smilacis Glabrae*, 40 parts of *Radix Astragali* Seu *Hedysari*, 15 parts of *Kochia scoparia* (L.) Schrad, 35 parts of *Carthamus tinctorius* L., 20 parts of *Cortex Radicis Dictamni Dasycarpi*, 15 parts of *Herba Ephedrae*, 25 parts of *Angelica sinensis*, 25 parts of *Rhizoma Ligustici* Chuangxiong, 15 parts of *Radix Rehmanniae*, 15 parts of *Ramulus*

*cinnamomi*, 20 parts of *Cynanchum otophyllum* Schneid, 10 parts of *Semen Sinapis Albae*, 10 parts of *Arisaema heterophyllum* Blume, 10 parts of *Typhonium blumei* Nicolson & Sivadasan, and 20 parts of *Radix Glycyrrhizae*.

The method for preparing the traditional Chinese medicine composition for the treatment of HFS after targeted drug treatment of the present example was carried out as follows:

(1) the medicinal materials was weighted according to the formula;
(2) the *Arisaema heterophyllum* Blume and the *Typhonium blumei* Nicolson & Sivadasan were crushed into a powdery mixture A; the other medicinal materials according to the formula were stirred, mixed, then crushed into a powdery mixture B;
(3) the powdery mixture A was added with distilled water 10 times of its volume, heated to 100° C., and decocted continuously for 50 min, then the powdery mixture B was added and decocted continuously for 35 min, cooled and filtered to obtain a cooling liquid and medicinal residues;
(4) the medicinal residues were added with distilled water 8 times of its volume, heated to 100° C., decocted continuously for 30 min, cooled and then filtered to obtain a filtrate; and
(5) the cooling liquid in step (3) and the filtrate in step (4) were combined, and a resulting mixed filtrate was centrifuged at 4000 g for 10 minutes at room temperature, a supernatant was collected, and the supernatant was concentrated to 1 g/ml, a resulting medicine solution was yellowish-brown, and had strong smell of traditional Chinese medicine, after sterilization and encapsulation, a traditional Chinese medicine composition for treating HFS after targeted drug treatment was obtained. The obtained traditional Chinese medicine had a liquid pharmaceutical dosage form.

90 cases were selected, including 48 males and 42 females. The youngest patient was 28 years old and the oldest was 69 years old, with an average age of 46 years. The cases were randomly divided into 9 groups according to age and condition, with 10 cases in each group. Efficacy was judged based on HFS grading, in which skin changes or dermatitis, paresthesias, and tissue destruction took the first place.

The traditional Chinese medicine composition of this example was used for treatment, and the dosage was as follows: for patients of 38-48 years old, 200 ml was used once a day to fumigate and wash the affected part; for patients of 49-69 years old, 200 ml was used for each fumigation and wash of the affected part twice a day. After one week of fumigation and washing, the HFS grade of 81% of the patients was decreased by one level (level 3 was decreased to level 2, and level 2 was decreased to level 1). After two weeks of fumigation and washing, 90% of patients with skin changes or dermatitis returned to normal basically, and sensory abnormalities disappeared basically. No obvious adverse reactions appeared in patient during treatment, and no adverse reactions of the test medicine were observed.

Example 4

A traditional Chinese medicine composition for treating HFS after targeted drug treatment was mainly prepared from the following components by weight: 30 parts of *Radix Sophorae Flavescentis*, 20 parts of *Herba Taraxaci*, 20 parts of *Flos Chrysanthemi Indici*, and 20 parts of *Herba Cum Radice Violae* Yedoensitis, 30 parts of *Rhizoma Smilacis Glabrae*, 60 parts of *Radix Astragali* Seu *Hedysari*, 10 parts of *Kochia scoparia* (L.) Schrad, 45 parts of *Carthamus tinctorius* L., 15 parts of *Cortex Radicis Dictamni Dasycarpi*, 5 parts of *Herba Ephedrae*, 25 parts of *Angelica sinensis*, 25 parts of *Rhizoma Ligustici* Chuangxiong, 30 parts of *Radix Rehmanniae*, 10 parts of *Ramulus cinnamomi*, 25 parts of *Cynanchum otophyllum* Schneid, 5 parts of *Semen Sinapis Albae*, 15 parts of *Arisaema heterophyllum* Blume, 15 parts of *Typhonium blumei* Nicolson & Sivadasan, and 30 parts of *Radix Glycyrrhizae*.

The method for preparing the traditional Chinese medicine composition for the treatment of HFS after targeted drug treatment of the present example was carried out as follows:

(1) the medicinal materials was weighted according to the formula;
(2) the *Arisaema heterophyllum* Blume and the *Typhonium blumei* Nicolson & Sivadasan were crushed into a powdery mixture A; the other medicinal materials according to the formula were stirred, mixed, then crushed into a powdery mixture B;
(3) the powdery mixture A was added with distilled water 10 times of its volume, heated to 100° C., and decocted continuously for 50 min, then the powdery mixture B was added and decocted continuously for 40 min, cooled and filtered to obtain a cooling liquid and medicinal residues;
(4) the medicinal residues were added with distilled water 8 times of its volume, heated to 100° C., decocted continuously for 35 min, cooled and then filtered to obtain a filtrate; and
(5) the cooling liquid in step (3) and the filtrate in step (4) were combined, and a resulting mixed filtrate was centrifuged at 4000 g for 10 minutes at room temperature, a supernatant was collected for vacuum concentration at 60° C., a resulting extract was freeze-dried to powder, and stored at −20° C. A traditional Chinese medicine composition for treating HFS after targeted drug treatment was obtained. The obtained traditional Chinese medicine had a pharmaceutical dosage form of Semi-solid powdered mixture. The powder was dissolved in water of equal volume, then heated to 45° C., mixed evenly for use. A resulting medicine solution was yellowish-brown, and had strong smell of traditional Chinese medicine.

150 cases were selected, including 80 males and 70 females. The youngest patient was 24 years old and the oldest was 87 years old, with an average age of 54 years. The cases were randomly divided into 15 groups according to age and condition, with 10 cases in each group. Efficacy was judged based on HFS grading, in which skin changes or dermatitis, paresthesias, and tissue destruction took the first place.

The traditional Chinese medicine composition of this example was used for treatment, and the dosage was as follows: for patients of 24-55 years old, 200 ml was used once a day to fumigate and wash the affected part; for patients of 56-87 years old, 200 ml was used for each fumigation and wash of the affected part twice a day. After one week of fumigation and washing, the HFS grade of 82% of the patients was decreased by one level (level 3 was decreased to level 2, and level 2 was decreased to level 1). After two weeks of fumigation and washing, 9% of patients with skin changes or dermatitis returned to normal basically, and sensory abnormalities disappeared basically. No obvious adverse reactions appeared in patient during treatment, and no adverse reactions of the test medicine were observed.

Example 5

A traditional Chinese medicine composition for treating HFS after targeted drug treatment was mainly prepared from the following components by weight: 20 parts of *Radix Sophorae Flavescentis*, 25 parts of *Herba Taraxaci*, 25 parts of *Flos Chrysanthemi Indici*, and 25 parts of *Herba* Cum Radice *Violae* Yedoensitis, 20 parts of *Rhizoma Smilacis Glabrae*, 45 parts of *Radix Astragali* Seu *Hedysari*, 20 parts of *Kochia scoparia* (L.) Schrad, 35 parts of *Carthamus tinctorius* L., 25 parts of *Cortex Radicis Dictamni Dasycarpi*, 10 parts of *Herba Ephedrae*, 15 parts of *Angelica sinensis*, 15 parts of *Rhizoma Ligustici* Chuangxiong, 20 parts of *Radix Rehmanniae*, 10 parts of *Ramulus cinnamomi*, 30 parts of *Cynanchum otophyllum* Schneid, 15 parts of *Semen Sinapis Albae*, 20 parts of *Arisaema heterophyllum* Blume, 20 parts of *Typhonium blumei* Nicolson & Sivadasan, and 40 parts of *Radix Glycyrrhizae*.

The method for preparing the traditional Chinese medicine composition for the treatment of HFS after targeted drug treatment of the present example was carried out as follows:

(1) the medicinal materials was weighted according to a formula;

(2) the *Arisaema heterophyllum* Blume and the *Typhonium blumei* Nicolson & Sivadasan were crushed into a powdery mixture A; the other medicinal materials according to the formula were stirred, mixed, then crushed into a powdery mixture B;

(3) the powdery mixture A was added with distilled water 10 times of its volume, heated to 100° C., and decocted continuously for 40 min, then the powdery mixture B was added and decocted continuously for 40 min, cooled and filtered to obtain a cooling liquid and medicinal residues;

(4) the medicinal residues were added with distilled water 8 times of its volume, heated to 100° C., decocted continuously for 35 min, cooled and then filtered to obtain a filtrate; and (5) the cooling liquid in step (3) and the filtrate in step (4) were combined, and a resulting mixed filtrate was centrifuged at 4000 g for 10 minutes at room temperature, a supernatant was collected, and the supernatant was concentrated to 1 g/ml, a resulting medicine solution was yellowish-brown, and had strong smell of traditional Chinese medicine, after sterilization and encapsulation, a traditional Chinese medicine composition for treating HFS after targeted drug treatment was obtained. The obtained traditional Chinese medicine had a liquid pharmaceutical dosage form.

80 cases were selected, including 46 males and 44 females. The youngest patient was 33 years old and the oldest was 66 years old, with an average age of 43 years. The cases were randomly divided into 8 groups according to age and condition, with 10 cases in each group. Efficacy was judged based on HFS grading, in which skin changes or dermatitis, paresthesias, and tissue destruction took the first place.

The traditional Chinese medicine composition of this example was used for treatment, and the dosage was as follows: for patients of 33-47 years old, 200 ml was used once a day to fumigate and wash the affected part; for patients of 48-66 years old, 200 ml was used for each fumigation and wash of the affected part twice a day. After one week of fumigation and washing, the HFS grade of 76% of the patients was decreased by one level (level 3 was decreased to level 2, and level 2 was decreased to level 1). After two weeks of fumigation and washing, 88% of patients with skin changes or dermatitis returned to normal basically, and sensory abnormalities disappeared basically. No obvious adverse reactions appeared in patient during treatment, and no adverse reactions of the test medicine were observed.

In summary, the traditional Chinese medicine composition of the present disclosure is used for the affected part of hand-foot skin after targeted drug treatment, has the effects of tonifying qi and nourishing blood, clearing heat and toxic materials, drying dampness and reducing phlegm. It has a good therapeutic effect on the HFS after targeted drug treatment, and is simple, convenient, cost effective and easy to implement.

What is claimed is:

1. A traditional Chinese medicine composition for treating hand-foot syndrome after targeted drug treatment, wherein the traditional Chinese medicine composition comprises consists of a decoction of the following components by weight: 20-50 parts of *Radix Sophorae Flavescentis*, 20-50 parts of *Herba Taraxaci*, 20-50 parts of *Flos Chrysanthemi Indici*, 20-50 parts of *Herba* Cum Radice *Violae* Yedoensitis, 20-50 parts of *Rhizoma Smilacis Glabrae*, 30-60 parts of *Radix Astragali* Seu *Hedysari*, 10-35 parts of *Kochia scoparia* (L.) Schrad, 10-45 parts of *Carthamus tinctorius* L., 15-45 parts of *Cortex Radicis Dictamni Dasycarpi*, 5-15 parts of *Herba Ephedrae*, 5-25 parts of *Angelica sinensis*, 5-25 parts of *Rhizoma Ligustici* Chuangxiong, 10-30 parts of *Radix Rehmanniae*, 5-15 parts of *Ramulus cinnamomi*, 10-30 parts of *Cynanchum otophyllum* Schneid, 5-15 parts of *Semen Sinapis Albae*, 5-20 parts of *Arisaema* heterophyllim Blume, 5-20 parts of *Typhonium blumei* Nicolson & Sivadasan, and 10-40 parts of *Radix Glycyrrhizae*.

2. The traditional Chinese medicine composition according to claim 1, wherein a mass ratio between the *Radix Sophorae Flavescentis* and the *Rhizoma Smilacis Glabrae* is 1:1.

3. The traditional Chinese medicine composition according to claim 1, wherein a mass ratio among the *Flos Chrysanthemi Indici*, *Herba Taraxaci* and *Herba* Cum Radice *Violae* Yedoensitis is 1:1:1.

4. The traditional Chinese medicine composition according to claim 1, wherein a mass ratio between the *Angelica sinensis* and the *Rhizoma Ligustici* Chuangxiong is 1:1.

5. The traditional Chinese medicine composition according to claim 1, wherein a mass ratio among the *Arisaema heterophyllum* Blume, the *Typhonium blumei* Nicolson & Sivadasan and the *Radix Glycyrrhizae* is 1:1:2.

6. A method for preparing the traditional Chinese medicine composition according to claim 1, comprising, (1) weighing medicinal materials according to a formula;

(2) crushing the *Arisaema heterophyllum* Blume and the *Typhonium blumei* Nicolson & Sivadasan into a powdery mixture A; stirring, mixing, and then crushing remaining medicinal materials according to the formula into a powdery mixture B;

(3) after adding water to the powdery mixture A for a period of decoction, adding the powdery mixture B for a period of continuous decoction, and conducting cooling and filtration to obtain a cooling liquid and medicinal residues;

(4) adding water to the medicinal residues for a secondary decoction, and conducting cooling and filtration to obtain a filtrate; and (5) combining the cooling liquid in step (3) and the obtained filtrate in step (4), and performing sterilization and encapsulation to obtain the traditional Chinese medicine composition.

7. The method according to claim 6, wherein, in step (3), after added with water, the powder mixture A is heated to boiling for decoction for 40-50 min.

8. The method according to claim 6, wherein in step (3), the powdery mixture B is added for decoction for 30-40 min.

9. The method according to claim 6, wherein in step (4), the secondary decoction is a continuous decoction for 30-40 min after a heating to boiling.

10. The method according to claim 6, wherein a mass ratio between the *Radix Sophorae Flavescentis* and the *Rhizoma Smilacis Glabrae* is 1:1.

11. The method according to claim 6, wherein a mass ratio among the *Flos Chrysanthemi Indici*, *Herba Taraxaci* and *Herba* Cum Radice *Violae* Yedoensitis is 1:1:1.

12. The method according to claim 6, wherein a mass ratio between the *Angelica sinensis* and the *Rhizoma Ligustici* Chuangxiong is 1:1.

13. The method according to claim 6, wherein a mass ratio among the *Arisaema heterophyllum* Blume, the *Typhonium blumei* Nicolson & Sivadasan and the *Radix Glycyrrhizae* is 1:1:2.

\* \* \* \* \*